United States Patent [19]

Wess

[11] 4,297,374

[45] Oct. 27, 1981

[54] SKIN MOISTURIZING AND CLEANSING CREAM

[76] Inventor: Beatrice M. Wess, 3590 Fenley Rd., Cleveland Heights, Ohio 44121

[21] Appl. No.: 83,597

[22] Filed: Oct. 11, 1979

[51] Int. Cl.³ .............................................. A61K 47/00
[52] U.S. Cl. .................................................. 424/364
[58] Field of Search ......................................... 424/364

[56] References Cited

U.S. PATENT DOCUMENTS

| | | | |
|---|---|---|---|
| 624,925 | 5/1899 | Grapevine | 424/364 |
| 1,516,562 | 11/1924 | Calabro | 424/364 |
| 1,631,384 | 6/1927 | Richmond | 424/364 |
| 3,810,996 | 5/1974 | Sutliff et al. | 424/364 |

FOREIGN PATENT DOCUMENTS 2388555 12/1978 France ................................ 424/364

*Primary Examiner*—Frederick E. Waddell
*Attorney, Agent, or Firm*—Meyer, Tilberry & Body

[57] ABSTRACT

A skin moisturizing and cleansing cream is produced by blending a quantity of fresh bananas or avocados with smaller amounts of baking powder, orange juice and solid or liquid vegetable shortening. The ingredients are blended to a creamy texture, and the cream is massaged into the skin by hand. Thereafter, the skin can be wiped with a dry paper or cloth towel, rinsed with warm water or, alternatively, the cream can be allowed to stay on the skin following the massaging. The skin cream is stored in a refrigerator between uses thereof.

13 Claims, No Drawings

SKIN MOISTURIZING AND CLEANSING CREAM

BACKGROUND OF THE INVENTION

This invention relates to the art of comestics and, more particularly, to an improved skin cleansing and moisturizing cream.

A number of creams and lotions are commercially available for cleansing and/or moisturizing the human skin, either in conjunction with bathing or washing the skin, as a preliminary procedure to bathing or washing the skin, or as a supplementary procedure following such bathing or washing. Some such creams and lotions contain abrasive materials for cleansing the skin and/or for removing dry, scaley skin, such as from the feet, elbows and hands of a user. While such creams serve the intended purposes, they often leave the user's skin dry following use thereof and, in the case of the removal of dry skin, they can irritate the skin of the user to the extent that the skin is tender to the touch. Other creams and lotions which do not include abrasive materials, but are intended for cleansing purposes, often include ingredients such as alcohol which tend to dry the user's skin, thus requiring supplemental application of a separate moisturizing cream or lotion to replace the moisture drawn from the skin. Still further, many cleansing lotions leave the skin of the user with an uncomfortably taut feeling, while moisturizing lotions often leave the skin with an excessively oily feeling to the touch. Still further in connection with commercially available cleansing and/or moisturizing creams and lotions, the latter often include ingredients which cause burning sensations on sensitive or chapped areas of a person's skin, or are irritating if applied close to the user's eyes.

SUMMARY OF THE INVENTION

In accordance with the present invention, an improved skin cleansing and moisturizing cream or lotion is provided, the ingredients of which enable cleansing of the skin of dirt and the like, the removal of dry skin, and the simultaneous moisturizing of the skin, all without causing irritation of the skin by excessive rubbing or scrubbing or causing irritation to the eyes if applied close thereto. Furthermore, the cream appears to lock in natural moisture in the skin during use, thus avoiding undesirable drying of the skin as a result of use thereof. More particularly, in accordance with the present invention, the cleansing and moisturizing cream is comprised of a blended mixture the major proportion of which is a fresh fruit, namely bananas or avocados, and the remainder of which is smaller amounts of baking powder, orange juice and vegetable shortening. These ingredients are blended together to form a creamy texture and, preferably, the mixture is kept refrigerated following the mixture thereof. The vegetable shortening is preferably a pure vegetable shortening and can be either liquid or solid, examples of liquid shortening being corn oil, peanut oil and soybean oil. The orange juice can be either natural orange juice or that derived from a frozen concentrate and, in the former case, the natural orange juice is preferably strained to remove any solids therein resulting from the squeezing operation. It is believed that the texture of the bananas or avocados provides an abrasive characteristic for cleansing purposes without the solid abrasive characteristic of pumice or the like which can result in skin irritation to the user. Additionally, the vegetable oil is believed to cooperate in the cleansing operation by lubricating dry skin and dirt, thus loosening the same for removal, and also serves to lock in natural skin moisture during the cleansing operation. The orange juice is believed to have a very minor drying effect which cooperates with moisturizing by the vegetable oil to leave the user's skin with a desired tautness after use of the cream. The baking powder provides a desired consistemcy to the cream.

A preferred composition is, by volume, a blended mixture of a predominant amount of bananas or avocados, the remainder being orange juice, vegetable shortening and baking powder, and in which the orang juice and shortening together provide the larger proportion of the remainder. The cream is prepared by placing the ingredients in a mixing receptacle, such as a motorized blender and, preferably, blending the ingredients for a period of about three to twelve minutes and, again preferably, sequentially at whipping and creaming speeds for about equal amounts of time. The blended mixture is preferably refrigerated between uses thereof, and is used by massaging a quantity thereof on and into the skin by hand. Following the massaging, the cream can be left on the skin without removal or, alternatively, can be wiped with a dry facial tissue or a paper or cloth towel, or the skin can be rinsed with warm water.

It is an object of the present invention to provide a skin moisturizing and cleansing cream which is particularly efficient with regard to providing a soft and smooth touch and appearance to the skin.

Another object is the provision of a skin moisturizing and cleansing cream which is particularly effective on dry skin for moisturizing the skin and removing skin residue through gentle massaging.

Still another object is the provision of a skin moisturizing and cleansing cream which, when massaged into the skin, provides a soft and smooth texture to the skin.

Still another object is the provision of a skin moisturizing and cleansing cream which is absorbed by the skin to provide a seal against drying of the skin.

Still another object is the provision of a skin moisturizing and cleansing cream which can be applied to sensitive skin areas and facial areas near the eyes without skin or eye irritation.

A further object is the provision of a skin moisturizing and cleansing cream all of the ingredients of which are edible food stuffs.

DESCRIPTION OF PREFERRED EMBODIMENTS

The skin moisturizing and cleansing cream of the present invention will be understood with reference to the following examples which are intended to exemplify the composition of the cream, the method of its preparation, and the method of its use.

EXAMPLE I

A fresh banana which, when cut, measures about 63 milliliters was placed in a household kitchen blender together with 15 milliliters of baking powder, 5 milliliters of orange juice prepared from a sugar free frozen orange juice concentrate, and 15 milliliters of a liquid pure vegetable shortening. The orange juice used is distributed in Cleveland, Ohio by the Wm. Edwards Company under the brand name Edwards. The shortening is distributed in Cleveland, Ohio by Fisher Foods, Inc. under the brand name Heritage House. The ingredients were first blended at a whipping speed for about three minutes and then at a creaming speed for about three minutes after which the mixture was placed in a refrigerator and stored for use. The texture of the mixture was very smooth and of heavy cream consistency. The mixture was used by several persons by massaging small amounts thereof totally into the skin including face, neck, elbows, hands and feet. After the massaging, the skin was either wiped lightly with dry facial tissues or a dry wash cloth, or hand rinsed lightly with warm water. The subjects, depending on the skin areas on which the cream was applied, found the cream to provide for the skin to have a texture which was smooth and soft to the touch with a desirable tautness to the skin, to provide protection to exposure to cold air when working out doors in the winter time, to moisturize areas of the skin which were dry and flaky such as after bathing or shaving, and to remove crusty skin residue from the feet when massaged thereinto and without any burning or tenderness of the feet following removal of the residue.

EXAMPLE II

Fresh bananas cut to provide a volume of about 500 milliliters was placed in a kitchen blender together with 60 milliliters of baking powder, 30 milliliters of orange juice prepared from the frozen concentrate used in Example I, and 68 milliliters of the pure liquid vegetable shortening used in Example I. The ingredients were mixed first at a whipping speed for about six minutes and then at a creaming speed for about six minutes, and the mixture was placed in the refrigerator for storage and use. The texture and consistency of the mixture was the same as that of Example I. Several subjects used the mixture in the manner set forth in Example I with the same results regarding the effects thereof on the skin.

EXAMPLE III

Fresh bananas cut to provide a volume of about 375 milliliters were placed in a kitchen blender and blended at low speed for five minutes after which 45 milliliters of baking powder and 60 milliliters of orange juice made from the frozen concentrate used in Example I were added to the blender. The ingredients then in the blender foamed and difficulty was encountered in getting the ingredients to mix using the blender. Blending was then done by hand to eliminate the foaming, after which 75 milliliters of the liquid vegetable shortening used in Example I were added and the blender again used. The final blending required first blending at a low speed, then a whipping speed, and then a creaming speed, the total mixing time from the blending of the bananas being about fifteen minutes. While difficulty was experienced in this procedure, the texture and consistency of the resulting cream was the same as that for the foregoing Examples as were the results upon use of the cream.

Example IV

Fresh bananas cut to provide a volume of about 250 milliliters were placed in a kitchen blender together with 90 milliliters of the pure liquid vegetable shortening used in Example I, 25 milliliters of baking powder and 75 milliliters of orange juice made from the frozen concentrate used in Example I. The ingredients were mixed progressively at whipping, beating and creaming speeds for a total time of about seven minutes after which the cream was refrigerated for storage and use. The texture of the cream was smooth and the cream could be poured from the blender. The results obtained upon use thereof were the same as those set forth with respect to the preceding Examples.

Example V

Fresh bananas cut to provide a volume of about 313 milliliters was placed in a kitchen blender together with 45 milliliters of the pure liquid vegetable shortening used in Example I, 15 milliliters of baking powder and 60 milliliters of orange juice made from the frozen concentrate used in Example I. The ingredients were mixed at a whipping speed for four minutes and then at a creaming speed for four minutes and then placed in a refrigerator for storage and use. The texture of the mixture was smooth and could be poured from the blender, and the results from use of the cream were the same as with the preceding Examples.

EXAMPLE VI

Fresh bananas cut to provide a volume of about 125 milliliters were placed in a kitchen blender together with 45 milliliters of the pure liquid vegetable shortening used in EXAMPLE I, 15 milliliters of baking powder and 30 milliliters of orange juice made from the frozen concentrate used in Example I. These ingredients were blended as in Example V and, as in Example V, the texture of the mixture was smooth and could be poured from the blender. Again, the results from use of the cream were the same as set forth in the preceding Examples.

Mixtures of the moisturizing and cleansing cream prepared in the same proportion of ingredients, but using fresh avocados in place of bananas have the same texture following blending and provide the same results with respect to use thereof on a person's skin. Likewise, mixtures using fresh orange juice as opposed to orange juice made from a frozen concentrate, and in which the fresh orange juice is strained to remove solid matter, have the same texture and consistency as the creams using orange juice from a concentrate, and provide the same results upon use of the cream on a person's skin. Still further, the use of a solid vegetable shortening, or liquid corn oil, peanut oil and soybean oil, in the proportions set forth in the Examples for the pure vegetable shortening does not change the texture of the cream or the results from the use thereof.

While it will be appreciated that a smooth texture is achieved through blending the ingredients in a motor driven blender, it will likewise be appreciated that the ingredients can be otherwise mixed, such as by a manually operated beater. Moreover, based on observation from the Examples set forth, it would appear that the consistency of the cream between pourable and non-pourable states is dependent primarily upon the amount of baking powder in the solution relative to the amounts of orange juice and shortening. In this respect, in Examples I, II and III the cream has a consistency requiring spooning for removal from the blender after mixing, and the ratio of orange juice and shortening to baking powder in these Examples is, respectively, 4:3, 5:3 and 3:1. In Examples IV, V and VI, on the other hand, the cream has a consistency which enables removal thereof from the blender by pouring after mixing, and in these Examples the ratio of orange juice and shortening to baking powder is, respectively, about 6.5:, 17:1, and 5:1.

Based on the foregoing Examples, and the total volume of ingredients in each of the cream mixtures thereof, the skin cream contains from about 36.8 to 76.0% bananas or avocados, about 3.5 to 15.3% baking powder, about 4.6 to 17.0% orange juice, and about 10.3 to 20.9% vegetable shortening. It will be appreciated that small amounts of dyestuffs can be added thereto for coloring purposes if desired and, likewise, that small amounts of perfume matter can be added to the cream to give a particular odor thereto. With regard to the latter, however, it has been found that the odor of the skin cream is not offensive, even after long periods of storage, although the color thereof may change due to the fruit content thereof.

In use of the skin cream, the latter is applied to desired areas of a person's body and massaged into the skin, and it will be appreciated that the amount of cream used and the massaging time are interdependent and determined, at least to some extent, by the dryness of the skin and the moisturizing effect desired by the user. In this respect, for example, it will be appreciated that less cream and less massaging generally would be required for application of the cream to the face for moisturizing and cleansing purposes than would be required in connection with moisturizing and removing dried skin residue from the feet or elbows of a user. Further in connection with use of the cream, it will be appreciated that the latter may be applied and massaged into the skin without any further treatment, thus assuring achieving maximum lubrication or moisturizing of the skin and protection from drying or chapping of the skin such as by exposure to outside air during the winter months. Alternatively, the cream can be massaged into the skin, such as the face, and the face wiped with a facial tissue or towel to remove dirt and dry skin residue from the face leaving the moisturizing effect of the cream in the skin. As yet another alternative, the cream can be massaged into the skin and the latter hand rinsed lightly with warm water to remove dirt and dry skin residue, the light rinsing providing for maximizing the moisturizing effect achieved. It has also been found that the cream can be applied to the skin prior to swimming to protect the skin from the drying effect caused by evaporation of water upon leaving a swimming pool. In this case, the cream is applied to the skin and lightly massaged thereacross before swimming.

While several specific examples have been set forth herein, it will be appreciated that these are merely exemplitive of the invention and not intended to be limiting, but rather to serve as a guide to those of ordinary skill in connection with the formulation and use of the skin cream.

Having thus described the invention, it is claimed:

1. A skin moisturizing and cleansing cream comprising by volume of mixture a predominant amount of fresh fruit selected from the group consisting of bananas and avocados, the remainder being orange juice, vegetable shortening and baking powder, and said orange juice and shortening together constituting the larger proportion of said remainder.

2. The skin cream according to claim 1, wherein said vegetable shortening is a liquid vegetable oil.

3. The skin cream according to claim 1, wherein said fruit is from about 56.8 to 76.0% of said mixture, said orange juice from about 4.6 to 17.0%, said shortening from about 10.3 to 20.9%, and said baking powder from about 3.5 to 15.3%.

4. The skin cream according to claim 3, wherein said vegetable shortening is a liquid vegetable oil.

5. A method of making a given volume of skin moisturizing and cleansing cream comprising, placing in a mixing receptacle, to provide said volume, a predominant amount of fresh fruit selected from the group consisting of bananas and avocados, and amounts of orange juice, vegetable shortening and baking powder for said orange juice and shortening together to be in an amount greater than said baking powder, and mixing said ingredients in said receptacle to a creamy texture.

6. The method according to claim 5, wherein said volume comprises from 56.8 to 76.0% of said fruit, from about 4.6 to 17.0% of said orange juice, from about 10.3 to 20.9% of said shortening, and from about 3.5 to 15.3% of said baking powder.

7. The method according to claim 6, wherein said mixing receptacle is a motor driven blender, and blending said ingredients for a period of from about three to twelve minutes.

8. The method according to claim 7, and blending said ingredients sequentially at a first speed and then a second speed higher than said first speed.

9. The method according to claim 8, and blending said ingredients about an equal amount of time at each said first and second speeds.

10. A method of moisturizing and cleansing skin comprising, massaging thereinto a blended mixture comprising by volume a predominant amount of a fresh fruit selected from the group consisting of bananas and avocados, the remainder being orange juice, vegetable shortening and baking powder, and said orange juice and shortening constituting the larger amount of said remainder.

11. The method according to claim 10, wherein said fruit is in about 56.8 to 76% of said mixture, said orange juice from about 4.6 to 17.0%, said shortening from about 10.3 to 20.9% and said baking powder from about 3.5 to 15.3%.

12. The method according to claim 10, further comprising wiping the skin with a dry towel after said massaging.

13. The method according to claim 10, further comprising rinsing the skin with warm water after said massaging.

* * * * *